United States Patent
Hatton

(10) Patent No.: US 11,593,900 B1
(45) Date of Patent: Feb. 28, 2023

(54) PORTABLE REMOTE PROCESSING APPARATUS FOR PROPERTY TRANSACTIONS

(71) Applicant: Wells Fargo Bank, N.A., San Francisco, CA (US)

(72) Inventor: Yvette Hatton, El Cerrito, CA (US)

(73) Assignee: Wells Fargo Bank, N.A., San Francisco, CA (US)

( * ) Notice: Subject to any disclaimer, the term of this patent is extended or adjusted under 35 U.S.C. 154(b) by 77 days.

(21) Appl. No.: 17/144,322

(22) Filed: Jan. 8, 2021

Related U.S. Application Data

(63) Continuation of application No. 15/472,365, filed on Mar. 29, 2017, now Pat. No. 10,929,938.

(51) Int. Cl.

| | |
|---|---|
| *G06Q 50/16* | (2012.01) |
| *G05B 15/02* | (2006.01) |
| *G01N 33/00* | (2006.01) |
| *G06Q 30/06* | (2012.01) |
| *F24F 11/30* | (2018.01) |
| *H04L 9/40* | (2022.01) |
| *G06Q 40/02* | (2012.01) |
| *G06Q 30/0601* | (2023.01) |
| *F24F 11/63* | (2018.01) |
| *F24F 11/62* | (2018.01) |

(52) U.S. Cl.
CPC .............. *G06Q 50/16* (2013.01); *F24F 11/30* (2018.01); *G01N 33/0036* (2013.01); *G05B 15/02* (2013.01); *G06Q 30/0627* (2013.01); *G06Q 40/025* (2013.01); *H04L 63/0861* (2013.01); *F24F 11/62* (2018.01); *F24F 11/63* (2018.01); *G05B 2219/2614* (2013.01); *G05B 2219/2642* (2013.01)

(58) Field of Classification Search
CPC .................................................. G06Q 50/163
See application file for complete search history.

(56) References Cited

U.S. PATENT DOCUMENTS

| | | | |
|---|---|---|---|
| 6,684,196 B1 | 1/2004 | Mini et al. | |
| 7,725,359 B1 * | 5/2010 | Katzfey | G06Q 30/0601 705/26.1 |
| 2012/0296863 A1 * | 11/2012 | Allison | G06F 3/0481 707/602 |
| 2015/0276238 A1 * | 10/2015 | Matsuoka | F24F 11/00 700/278 |
| 2016/0162772 A1 * | 6/2016 | Curtis | G06V 30/2247 345/8 |
| 2017/0228839 A1 * | 8/2017 | Motta | G06Q 50/16 |

* cited by examiner

*Primary Examiner* — Julie M Shanker
(74) *Attorney, Agent, or Firm* — Merchant & Gould P.C.

(57) ABSTRACT

A portable remote processing apparatus facilitates various aspects of a transaction, such as a real estate property transaction. A seller of the real estate property can use the portable remote processing apparatus to prepare a walk-through of the property for prospective buyers, to configure the property for a showing, and/or to interact with a buyer device to negotiate a sale of the real estate property. Typically, the portable remote processing apparatus communicates with a remote server device, thereby limiting the amount of hard coding in the apparatus and improving the processing capability of the apparatus.

1 Claim, 7 Drawing Sheets

PORTABLE REMOTE PROCESSING APPARATUS FOR PROPERTY TRANSACTIONS

INTRODUCTION

Arm's length property transactions typically involve multiple actors, such as sellers, buyers, agents for the sellers and/or buyers, lenders, and notaries public. Actual negotiations between buyers and sellers usually pass via agents. Each communication between parties can decrease the chance that an agreement is reached because of time delays and involvement of the agents.

SUMMARY

Embodiments of the disclosure are directed to a portable remote processing apparatus in property transaction systems. In one aspect, a portable remote processing apparatus includes a housing, a processing unit supported by the housing, a communication arrangement supported by the housing, and system memory. The system memory includes instructions that, when executed by the processing unit, cause the apparatus to: facilitate a walk-through of a property for sale via the communication arrangement, receive sale data from a seller device of the property for sale, and communicate with a buyer device, including negotiation of a sale price of the property for sale using the sale data.

In another aspect, a system includes a server computer, a database in communication with the server computer, and a portable processing apparatus. The portable processing apparatus includes a housing, a processing unit supported by the housing, a communication arrangement supported by the housing and including a biometric authentication unit, and memory. The memory includes instructions that, when executed by the processing unit, cause the portable processing apparatus to: facilitate a walk-through of a property for sale via the communication arrangement, receive sale data from a seller device of the property for sale, communicate with a buyer device, including negotiation of a sale price of the property for sale using the sale data, prepare the property for sale for a showing, and receive biometric authentication data.

In yet another aspect, a portable remote processing apparatus includes a housing, a processing unit supported by the housing, a communication arrangement supported by the housing and including a display unit and a biometric authentication unit, an electronic nose configured to obtain an air sample within a property for sale, and system memory. The system memory includes instructions that, when executed by the processing unit, cause the apparatus to: facilitate a walk-through of the property for sale via the communication arrangement, receive sale data from a seller device of the property for sale, communicate with a buyer device, including negotiation of a sale price of the property for sale using the sale data, determine whether one or more of the following is present in the air sample: mold, pet dander, and smoke, and prepare the property for sale for a showing, which includes enabling access to the property for a potential buyer and logging a buyer identifier indicating an identity of the potential buyer. The memory also includes instructions that when executed by the processing unit, cause the apparatus to: receive biometric authentication data, communicate offer details to the seller device in real time, receive a message from the seller device, the message including an indication whether the offer details are acceptable, and transmit the offer details to a loan provider.

The details of one or more embodiments are set forth in the accompanying drawings and the description below. Other features, objects, and advantages of these embodiments will be apparent from the description, drawings, and claims.

DESCRIPTION OF THE DRAWINGS

The following drawing figures, which form a part of this application, are illustrative of described technology and are not meant to limit the scope of the disclosure in any manner.

DETAILED DESCRIPTION

Broadly, the present disclosure is directed to improving, facilitating, and expediting transactions. In particular, examples disclosed relate to a low-cost apparatus provided to a seller of real estate property. The apparatus includes a set of pre-programmed, specialized logic configured to facilitate various aspects of a real estate property transaction.

One or more remote servers, in communication with one or more databases, receive and process requests from the apparatus. Typically, the apparatus transmits the requests to the remote server(s) over a network, such as the internet. By communicating with a remote server, the processing capability of the apparatus is improved. Further, because the apparatus leverages a remote server for processing, the amount of hard coding in the apparatus is limited.

Figure 1:
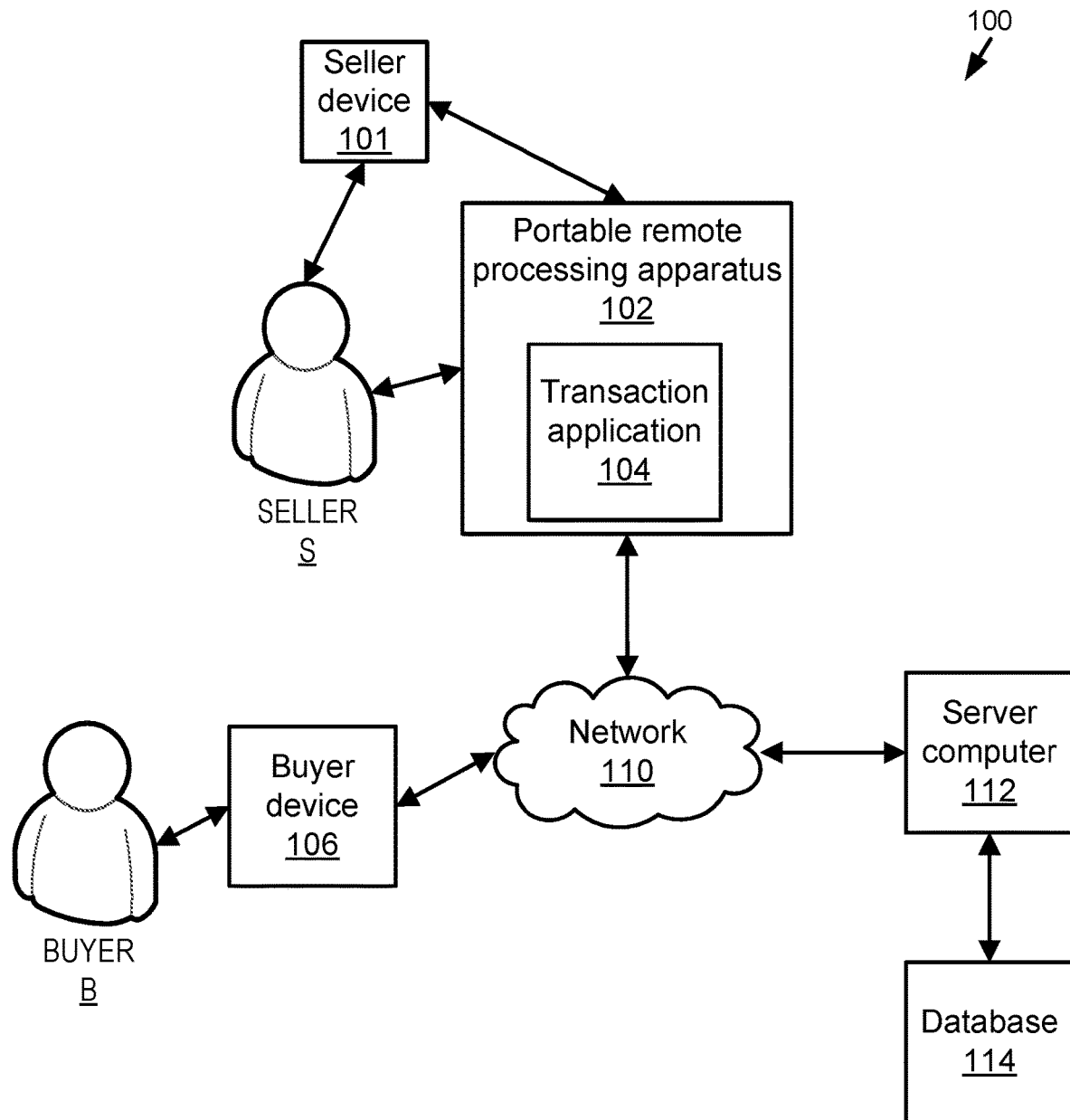
FIG. 1 is a schematic diagram of an example system for facilitating a property transaction.

FIG. 1 is a schematic diagram of an example system 100 for facilitating a property transaction. Example system 100 includes portable remote processing apparatus 102 that facilitates various aspects of typical property transactions, including home preparation, showing, and sale interaction. Example system 100 also includes seller device 101, buyer device 106, network 110, server computer 112, and database 114. Seller S interacts with portable remote processing apparatus 102. Buyer B is associated with and uses buyer device 106 to communicate with portable remote processing apparatus 102 via network 110. Other embodiments can include more or fewer components.

Seller S is a property owner or agent (e.g., realtor) associated with the property owner. As part of the sale process, seller S acquires portable remote processing apparatus 102, which can be provided by various entities such as a loan provider. Seller S interacts with portable remote processing apparatus 102 to communicate with and program various attributes of portable remote processing apparatus 102. Usually, seller S uses a computing device, such as seller device 101, to interact with portable remote processing apparatus 102.

Portable remote processing apparatus 102 facilitates a selling process for seller S and the buying process for buyer B by coordinating and negotiating processes typically associated with a sale of property. Portable remote processing apparatus 102 is typically a relatively small apparatus, hand-held size for example, with limited processing power and minimal hard coding in its memory. Most of the processing is performed by server computer 112, which interacts with database 114, and communicates with portable remote processing apparatus 102 over network 110. Portable remote processing apparatus 102 can additionally include a global positioning system (GPS) unit capable of communicating with GPS systems and acquiring position coordinates.

Portable remote processing apparatus 102 includes transaction application 104 which guides and executes various processes of the property transaction. For instance, transaction application 104 includes various modules to configure a property for sale, to interact with a buyer, and to perform post-agreement operations. Additional details about transaction application 104 are discussed below with reference to FIG. 2.

When seller S is showing a property for sale, seller S leaves portable remote processing apparatus 102 somewhere within the property for sale such that it is able to communicate with buyer device 106. Portable remove processing apparatus 102 can communicate with buyer device 106 to, for example, enable access to the property, validate or verify buyer B and/or buyer device 106, negotiate a sale price, communicate with seller S about the negotiation, and negotiate contingencies.

Buyer device 106 is typically a portable computing device capable of communicating over a network 110 such as Wi-Fi, Bluetooth and the like. Example buyer devices 106 include smartphones, tablet computers, smartwatches, etc. In some instances, buyer device 106 has been associated with the property for sale and/or portable remote processing apparatus 102 prior to buyer B's entrance into the property.

One or more components of environment 100 are in communication with each other via network 110. Network 110 may include any type of wireless network, a wired network, or any communication network known in the art. For example, wireless connections can include cellular network connections and connections made using protocols such as 802.11a, 802.11g, 802.11n, and/or 802.11ac. In other examples, a wireless connection can be accomplished directly between portable remote processing apparatus 102 and buyer device 106 using one or more wired or wireless protocols, such as Bluetooth, Bluetooth Smart, Wi-Fi Direct, radio-frequency identification (RFID), or Zigbee. Other configurations are possible.

The example server computer 112 is a computing device of an entity, such as a financial institution or other third party. In the examples described herein, the server computer 112 can be used to request, process, and store information from portable remote processing apparatus 102. This information can be used to facilitate a transaction for the property for sale.

The example database 114 is a database associated with the server computer 112. The server computer 112 can query the database 114 to access and store information related to the property for sale. For example, as described further below, information regarding the property for sale can be obtained from the portable remote processing apparatus 102. The server computer 112 can store this information in the database 114 using various methods, such as a blockchain recording system. Other configurations are possible.

Figure 2:
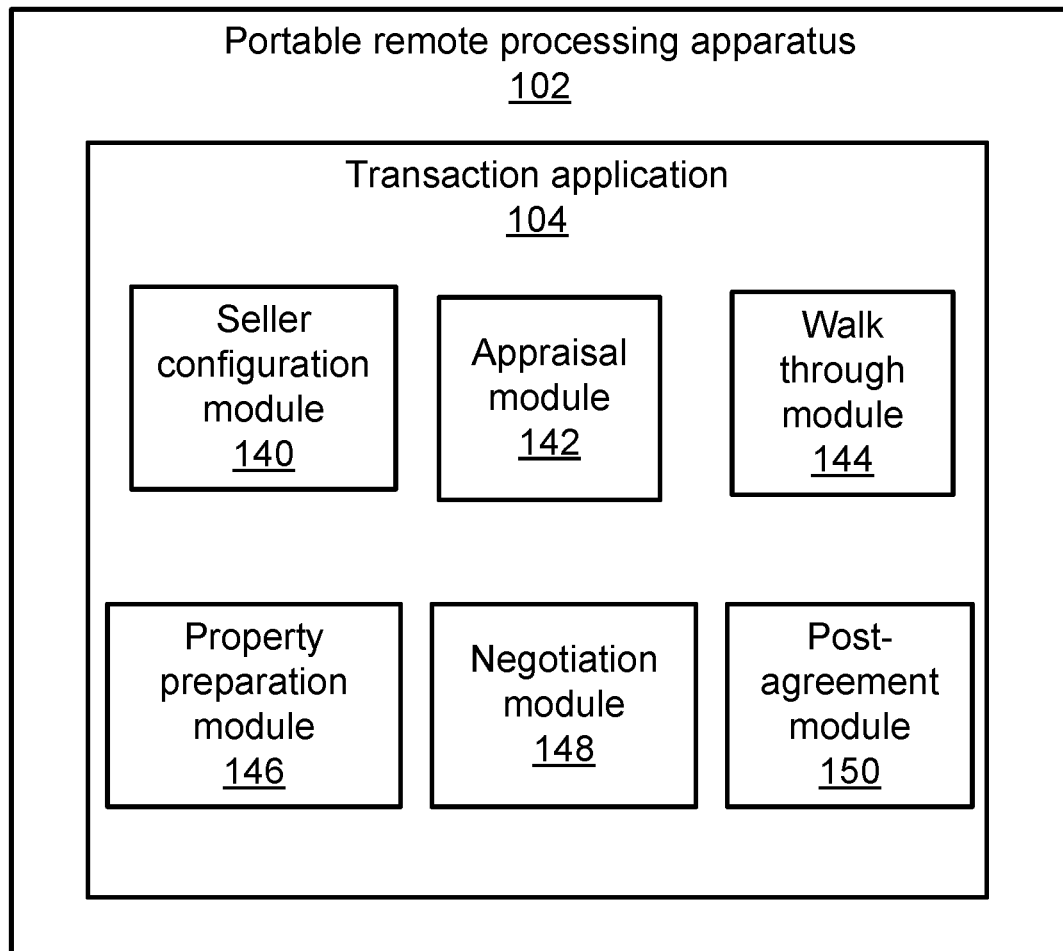
FIG. 2 shows example modules provided by the portable remote processing apparatus of FIG. 1.

FIG. 2 shows logical components of transaction application 104. Transaction application 104 is typically hosted on portable remote processing apparatus 102. In the example, transaction application 104 includes seller configuration module 140, appraisal module 142, walk through module 144, property preparation module 146, negotiation module 148 and post-agreement module 150. Other embodiments can include more or fewer components.

Portable remote processing apparatus 102 is programmed to execute one or more of modules 140, 142, 144, 146, 148, 150, according to firmware and/or software accessible to portable remote processing apparatus 102. For example, a processing unit of portable remote processing apparatus 102 executes software stored on computer readable media to implement modules 140, 142, 144, 146, 148, 150.

Seller configuration module 140 interacts with seller S to validate, authenticate, and prepare for sale of the property. For instance, seller configuration module 140 requests a seller name, property address, and other identifying indicia of seller S. In this way, portable remote processing apparatus 102 verifies that seller S is the person, or an agent of the person, who requested apparatus 102. Seller S can also be authenticated by seller configuration module 140 through one or more biometric data acquisitions, such as an iris scan and/or fingerprint acquisition.

In addition to verifying a seller S's identity, seller configuration module 140 also identifies property details. Property details include attributes of the property, such as square footage, bedrooms, bathrooms, number of floors, and/or general layout of each floor of the property. Property data can be acquired through seller's S interaction with transaction application 104. Alternatively, transaction application 104 can, upon receiving an address, MLS listing number or other identifying indicia of the property, request specific data about the property from server computer 112.

Seller configuration module 140 can also learn about one or more smart devices within the property for sale. Example smart devices include smart thermostats, Wi-Fi or Bluetooth enabled stereo systems, smart lighting systems, smart door locks, window shades operable remotely, fireplaces operable remotely, smart appliances, and the like. In some instances seller configuration module 140 may require additional input from seller S to properly configure and/or communicate with the one or more smart devices within the property.

Seller configuration module 140 also prompts for sale details from seller S. One or more of these details are used by transaction application 104 to negotiate with prospective buyer B. For example, details regarding the sale of the property can include minimum sale price, acceptable sale price, ideal sale price, ideal closing date, as well as unacceptable price ranges, unacceptable closing dates, and unacceptable contingencies.

Appraisal module 142 facilitates an appraisal by portable remote processing apparatus 102. Generally, the appraisal provided by portable remote processing apparatus 102 is based on numerous inputs, such as property status information captured by portable remote processing apparatus 102, traditional appraisal inputs, and virtual inspections of the property.

Example property status information can be pulled from sensors or other computing devices positioned about the property for sale, such as heating, ventilation and air conditioning (HVAC) sensors coupled to heating and/or cooling units, temperature control units, and other sensors configured to obtain property status information. Example traditional appraisal inputs include the estimated market value of the property, along with other information like disclosures of significant features (number of bedrooms, bathrooms, square footage, floor plans, location maps, pictures, etc.) and issues (e.g., former flooding and other damage, etc.) associated with the house and comparable property values.

Appraisal module 142 can also provide a virtual inspection of the property. Such virtual inspections could include inspections by potential purchasers and of the property and/or inspections by owners of the property. The virtual inspection allows individuals who cannot visit the property to assess aspects of the property, both visually and through the property status information captured by the appraisal module 142.

Walk through module 144 facilitates a buyer walk through of the property for sale. In some instances, walk through module 144 can guide a prospective buyer through the house and comment or educate the buyer about interesting or valuable aspects of the property for sale. During inspection of the house, when the seller S walks portable remote processing apparatus 102 about the property, seller S can provide notes or comments about various aspects of the property. These notes and comments can be replayed during the buyer walk through.

Portable remote processing apparatus 102 can be configured to provide information during the walkthrough based on its location within the property. Location determination can be accomplished in various ways. For example, a location about the property can be determined using GPS or triangulation based upon two or more wireless signals (e.g., Wi-Fi, cellular, Bluetooth, etc.). Location determination can also be based upon devices positioned within each room or location of the property for sale, such as barcodes that can be scanned or near-field communication (NFC) tags that can be communicated with.

Property preparation module 146 prepares the property for viewing by one or more prospective buyers. Upon receiving data regarding showings of the property, property preparation module 146 can be configured to adjust various environmental aspects of the property so that the property is in desirable condition when buyer B arrives. Example preparation operations include: adjusting the temperature of the property to be within comfortable ranges for human occupants, turning on a stereo at an appropriate volume, raising and/or lowering window shades, turning on a fireplace, and turning on an oven to bake cookies therein, as well as turning the oven off.

Property preparation module 146 can also include preliminary buyer device interactions. For a house outfitted with smart door locks, property preparation module 146 can unlock doors for buyer device upon buyer device authentication. Property preparation module 146 can also establish a communication with buyer device 106. Buyer device 106 authentication can also include verifying the identity of buyer B.

Negotiation module 148 manages communication with buyer device 106 during negotiation of sale price and contingencies. Negotiation module 148 performs some initial processing of messages received from buyer device 106 locally before transmitting messages to server computer 112. Typically, server computer 112 receives and processes messages from negotiation module 148 during negotiation. Most or all decisions during negotiation are made by server computer 112 and then transmitted to portable remote processing apparatus 102.

Negotiation module 148 can provide a graphical user interface (GUI) displayed by buyer device 106. The GUI allows the buyer B to enter offer terms and submit those terms to portable remote processing apparatus 102. Then, another GUI provided on seller device 101 presents the offer and any other terms from the buyer B. Seller S can review the offer and terms and the GUI on seller device 101 enables seller S to accept or provide counter offers.

Another alternative is that buyer B enters offer data in the GUI as free form text. A text-parsing engine provided by server computer 112 reviews the free form text to identify particular offers or offer details. Then those details are provided to seller device 101. Example negotiating techniques performed by negotiation module 148 are discussed below with reference to, at least, FIGS. 4-6.

Post-agreement module 150 manages various actions after seller S and buyer B reach agreement about the sale. For instance, post-agreement module 150 can request (from server computer 112) contractual forms and transmit those forms to buyer device 106 and to the seller. Additionally, post-agreement module 150 can interface between buyer B and one or more lenders. Post-agreement module 150 can also act as an e-notary and provide validation (e.g., by obtaining biometric data) necessary for execution of forms related to the property transaction.

Figure 3:
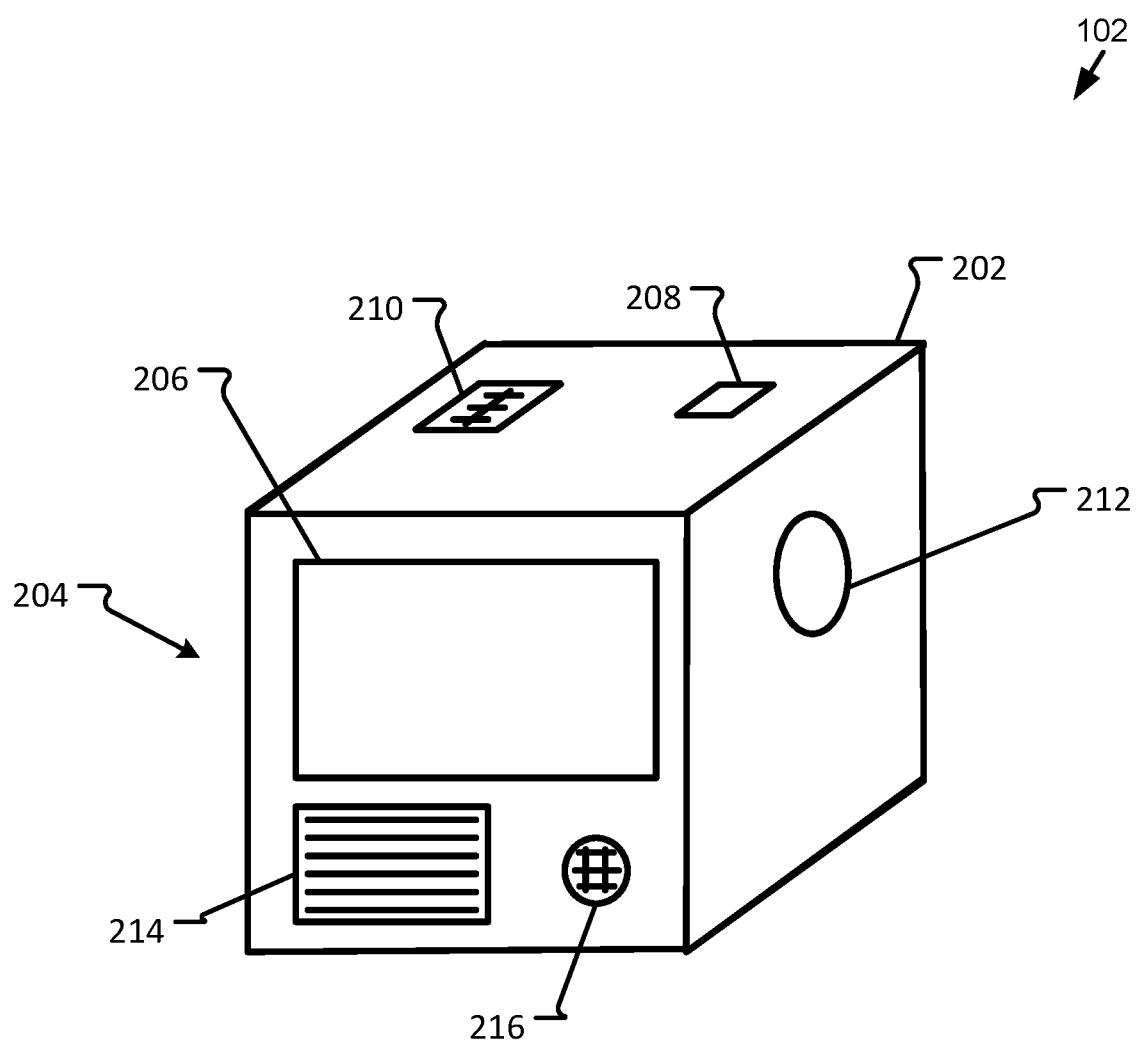
FIG. 3 shows an example portable remote processing apparatus used in the system of FIG. 1.

FIG. 3 shows an example portable remote processing apparatus 102. Generally, portable remote processing apparatus 102 is an apparatus small enough to be held and light-weight enough to be carried around a house or property for sale. Remote processing apparatus 102 includes various components designed to, for instance, receive information from a seller, obtain data about the property for sale, communicate with the buyer, and communicate with remote server computer 112. Other embodiments can include more or fewer components than what is shown in FIG. 3.

Portable remote processing apparatus 102 includes housing 202. As shown, housing 202 is cubical. However in other instances housing 202 can be other shapes. For instance, housing 202 can alternatively be spherical, pyramidal or polyhedral.

Portable remote processing apparatus 102 also includes communication arrangement 204. Communication arrangement 204 includes components configured to interact with seller S, buyer B, and/or buyer device 106. Communication arrangement 204 can include display unit 206.

Display unit 206 is typically a liquid crystal display or the like, and is in communication with a processing unit and memory that are within housing 202. The processing unit and memory are not shown in FIG. 3. Display unit 206 can display various messages to seller S and buyer B. For instance, display unit 206 can provide guidance to seller S during an appraisal process, or guidance to buyer B during a walk-through process. Display unit 206 can also be used during configuration processes and to show communication status between remote processing apparatus 102 and components in example system 100 discussed above.

Radio 208 enables portable remote processing apparatus 102 to communicate with various components of example system 100. In some instances, portable remote processing apparatus 102 includes more than one type of radio 208. Example radios include Wi-Fi radios, Bluetooth radios, and the like.

Portable remote processing apparatus 102 also includes electronic nose 210. Electronic nose 210 receives and processes particles present in the air. For instance, molecules that are attributable to odors or smells within the property can be detected by electronic nose 210 and their identity confirmed upon processing. An example electronic nose is the EN EOS835 (SACMI Imola S.C., Imola, Italy). In particular, electronic nose 210 is used to detect in the air: fire residue, mold, and/or pet dander.

Camera 212 is also supported by housing 202 and receives images of the property as well as images used for authentication. For example, camera 212 can be used to capture photographs of the property during an appraisal process or during the walk-through, which can be later transmitted to buyer B or seller S. Camera 212 can also be used to acquire biometric data. Example biometric data include fingerprints and iris scans.

Communication arrangement 204 also includes speaker 214 and microphone 216, both supported by housing 202. Speaker 214 can be used to communicate with seller S and/or buyer B during the walk-through and appraisal processes. Usually, however, communication about negotiation and sale prices are transmitted between devices and not spoken to buyer B or seller S. Microphone 216 can be used by seller S to add notes during the appraisal, which can be later communicated to buyer B during a walk-through of the property. Additionally microphone 216 can be used to detect and/or determine whether any unnatural ambient noise is present or detectable within the property for sale.

Figure 4:
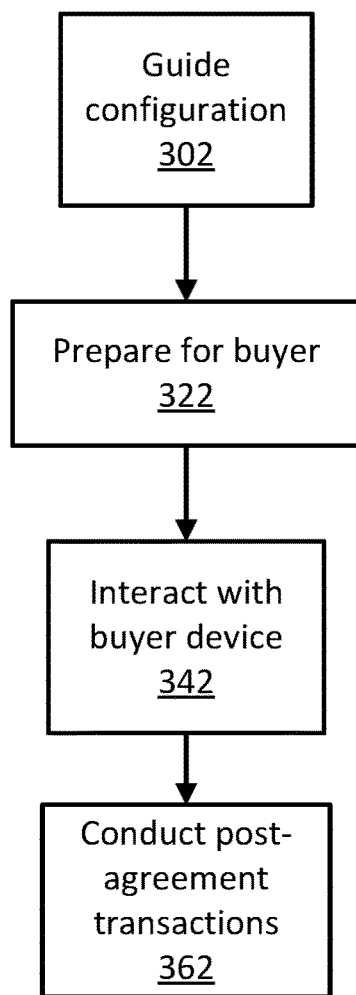
FIG. 4 shows an example method for facilitating property sale using the system of FIG. 1.

FIG. 4 shows an example flow chart of a method 300 for facilitating property sale. The example method 300 includes guiding configuration (operation 302), preparing for a buyer (operation 322), interacting with a buyer device (operation 342), and conducting post-agreement transactions (operation 362). Example method 300 is from the perspective of remote processing apparatus 102 shown and described with reference to FIG. 1 above. Other embodiments can include more or fewer operations.

Figure 5:
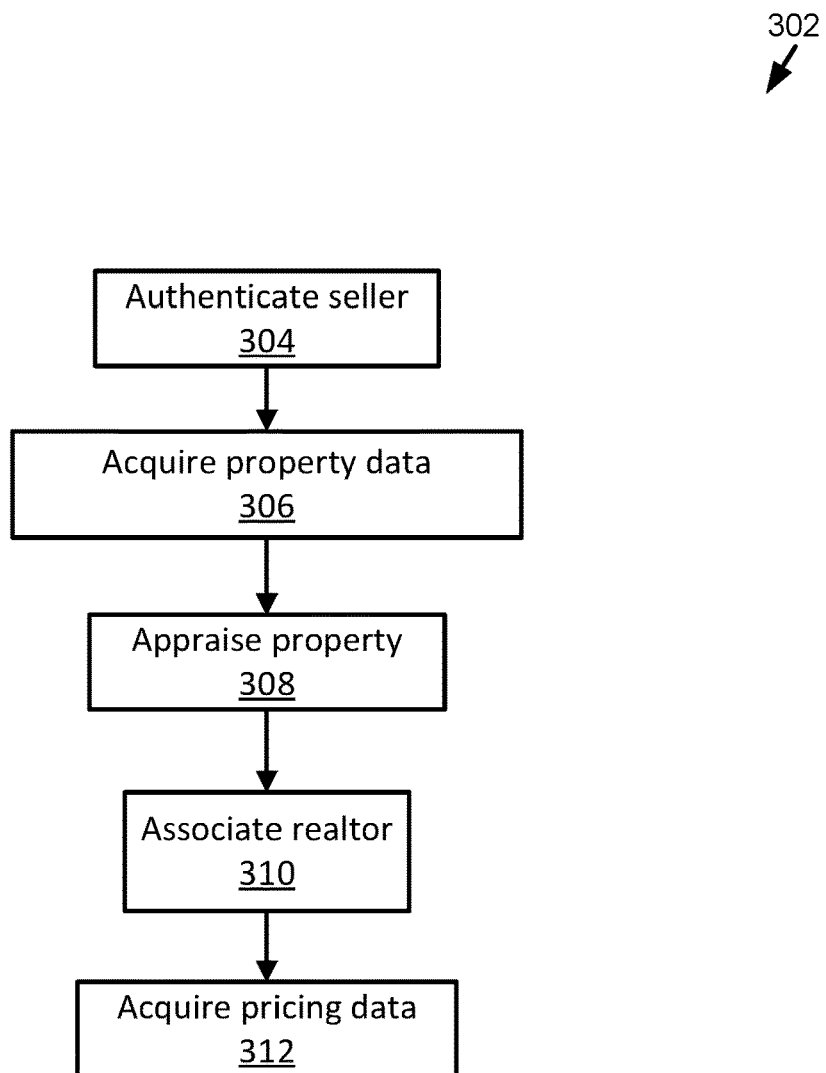
FIG. 5 shows example processes part of the guiding configuration operation shown in the method of FIG. 4.

Referring to FIG. 5, aspects of guiding configuration (operation 302) are provided. Guiding configuration 302 includes authenticating seller (operation 304), acquiring property data (operation 306), appraising property (operation 308), associating a realtor (operation 310), and acquiring pricing data (operation 312). Guiding configuration (operation 302) begins by authenticating the seller (operation 304). As discussed above, typically a real estate property seller requests portable remote processing apparatus 102 from a third party, such as a prospective lender. Portable remote processing apparatus 102 may or may not be preconfigured for a particular seller of that property before the seller receives the apparatus. Accordingly, the seller is authenticated before the seller can configure the apparatus to sell or facilitate the sale of the property.

Authenticating the seller (operation 304) can be performed in a number of ways. As one example, the seller may enter a user name and password that are associated with the seller at the lender. In some instances, a one-time passcode can additionally be used for verification or authentication purposes. Also, a seller can provide their fingerprint and/or iris data to verify against fingerprint or iris data already in the database and associated with the seller. In some embodiments, the seller authentication can be postponed and other operations of example method 300 conducted, up to, but not including, consummation of a contract or agreement between the parties.

After authenticating the seller (operation 304), property data are next acquired (operation 306). Example property data include square footage, number of bedrooms, bathrooms, floors, property taxes, year constructed, and the like. Portable remote processing apparatus 102 can acquire property data from the seller and/or seller device 101. Acquiring property data (operation 306) can also be performed by pulling data from one or more databases by computer server 112.

Guiding configuration (operation 302) also includes appraising the property (operation 308). Appraising the property (operation 308) includes acquiring property status information and can also include an inspection of the property by portable remote processing apparatus 102. That inspection can include the seller providing notes or comments about the property which can be used during a potential buyer walkthrough.

As discussed above with reference to FIG. 2, the appraisal inputs used for appraising the property (operation 308) can include property data from operation 306, data from the inspection, and data obtained from one or more sensors and/or computing devices about the property.

Optionally, guiding configuration (operation 302) can include associating a realtor (operation 310) with the property for sale. Upon entering a realtor name and/or contact information, portable remote processing apparatus 102 can go about verifying the realtor, such as through email confirmation links. After a realtor is associated with the property, various privileges can be granted to the realtor. Example privileges include unlocking and locking the property, controlling various smart appliances within the property, and indicating assent to offer terms on behalf of the seller.

Next, portable remote processing apparatus 102 acquires pricing data (operation 312). Pricing data can include ranges of prices for the property, and also include asking prices various levels to step down if the buyer does not accept earlier offers, and bottom line prices below which the seller is not willing to go. In some instances, pricing data can also include appliances or parts of the house that the seller is willing to negotiate about to secure a deal. For example, a hot tub, clothes washer and dryer, or other removable objects within the property.

Figure 6:
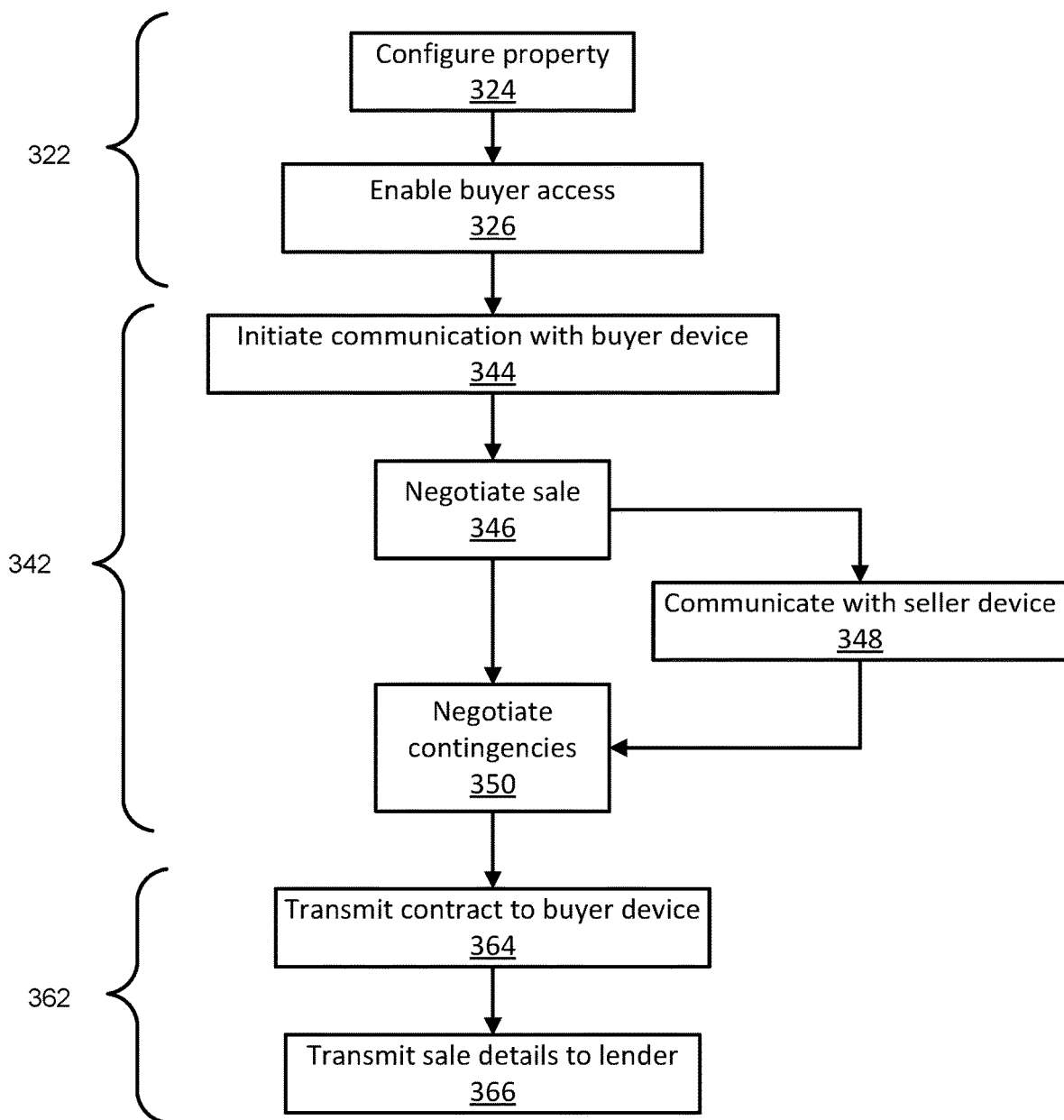
FIG. 6 shows example processes for the preparing for a buyer, interacting with a buyer device, and conducting post-agreement transactions operations shown in the method of FIG. 4.

FIG. 6 provides example processes for preparing for a buyer (operation 322), interacting with a buyer device (operation 342), and conducting post-agreement transactions (operation 362). Preparing for a buyer (operation 322) typically includes configuring a property (operation 324) and enabling buyer access (operation 326). In many instances, the property for sale is not in a condition for showing when the owner is not present and when no buyers are within the property. It is often desirable to have the property in a condition such that it is welcoming, warm, and makes the buyer feel like it is a place they would like to spend their time. Accordingly, configuring the property (operation 324) can include actions to make the property for sale desirable to various prospective buyers.

Example actions of configuring a property (operation 324) include communicating with lighting units in the property for sale. In some properties, one or more lighting units are configurable remotely and possibly in communication with a Wi-Fi network. In those instances, the portable remote processing apparatus 102 can turn on one or more lighting units before the buyer arrives at the property. Additionally, configuring the property (operation 324) can include communicating with a fireplace unit to turn on the fireplace. Still further, another example is instructing a Wi-Fi enabled thermometer to warm or cool the property to a comfortable temperature range. Other configurations possible in operation 324 include communicating with a speaker arrangement to play music over speakers and turning on an oven that is Wi-Fi configured to bake contents therein, such as cookies.

Enabling buyer access (operation 326) can be dictated by communications from the buyer agent or the seller to the portable remote processing apparatus 102 corresponding to a particular time for showing of the property. Properties having smart locks can receive instructions from portable remote processing apparatus 102 (e.g., through Bluetooth, Wi-Fi, etc.) to unlock one or more doors at the time of the showing. Additionally, portable remote processing apparatus 102 can log buyer identifiers indicating an identity of the potential buyer who is viewing the property.

Interacting with buyer devices (operation 342) includes initiating communication with buyer devices (operation 344), negotiating a sale (operation 346), and negotiating contingencies (operation 350). Initiating communication with a buyer device (operation 344) includes establishing a connection and/or secured connection between the portable remote processing apparatus and a buyer device. For example, a secure Bluetooth connection or Bluetooth smart connection between the portable remote processing apparatus and buyer device can be established. In some instances, the seller or seller agent provides a buyer with a passcode or other identifier, and the buyer uses that identifier when connecting their device to the portable remote processing apparatus 102.

Next, a sale can be negotiated with the buyer device (operation 346). Negotiating a sale (operation 346) can include walking the buyer through the property based on instructions and comments made by the seller. Additionally, negotiating the sale (operation 346) includes prompting the buyer device for an offer or asking for assent to the list price of the property. Each time communication is received from the buyer device, those offer details, or other communications, can be transmitted to the seller device (operation 348). In some instances, portable remote processing apparatus 102 continues a negotiation without further input from the seller device. Alternatively, portable remote processing application 102 can be configured to require authentication and/or direction from seller device before proceeding with negotiation.

During the sale negotiation (operation 346), a variety of negotiation tactics can be used based on prior input from the seller. One tactic is binary: either the offer is acceptable or not and no further negotiations take place. As another example, portable remote processing apparatus 102 may be limited to keeping the list price the same, but offering various appliances or items within the property as a way to secure agreement. As another example, portable remote processing apparatus 102 can continue to decrease the sale price by pre-determined increments, ultimately reaching a pre-determined minimum, as possible ways to receive agreement from the buyer device as to a purchase price. These one or more counter-offers to the buyer device can be pre-set by the seller and/or are part of a negotiation algorithm provided by the remote server computer 112.

As part of the sale negotiation (operation 346), or separately after sale negotiation, one or more contingencies may be negotiated (operation 350). Example contingencies include move-in dates, closing dates, items in the property the buyer wishes to remain, agreements to repair various parts of the property, and the like. These contingencies can be communicated to the seller device for ascent.

One or more post-agreement transactions can be conducted (operation 362) after an agreement between buyer and seller is reached. These post-agreement transactions include transmitting a contract to a buyer device (operation 364) and transmitting sale details to a lender (operation 366). In some instances, after the buyer and seller have agreed on a price and contingencies, the remote server computer transmits a contract to portable remote processing apparatus 102, which in turn transmits the contract to the buyer device. The contract can include the ability for the buyer to electronically sign the document and may include electronic notary provisions, such as obtaining biometric data of the buyer by the portable remote processing apparatus 102. For example, in order to execute the contract, portable remote processing apparatus 102 prompts the buyer to provide an iris scan and/or fingerprint scan.

Additionally, the sale details and/or the contract can be transmitted to a lender (operation 366). In some instances, the sale details may be transmitted to multiple potential lenders on behalf of the buyer to solicit multiple bids for providing funding for the loan. The lender may be the same entity that provided the portable remote processing apparatus to the seller. Further, the detail-forwarding functionality can be limited to only transmit sale details to the lender who provided the portable remote processing apparatus, as a way to encourage the buyer to use that lender for the transaction.

Figure 7:
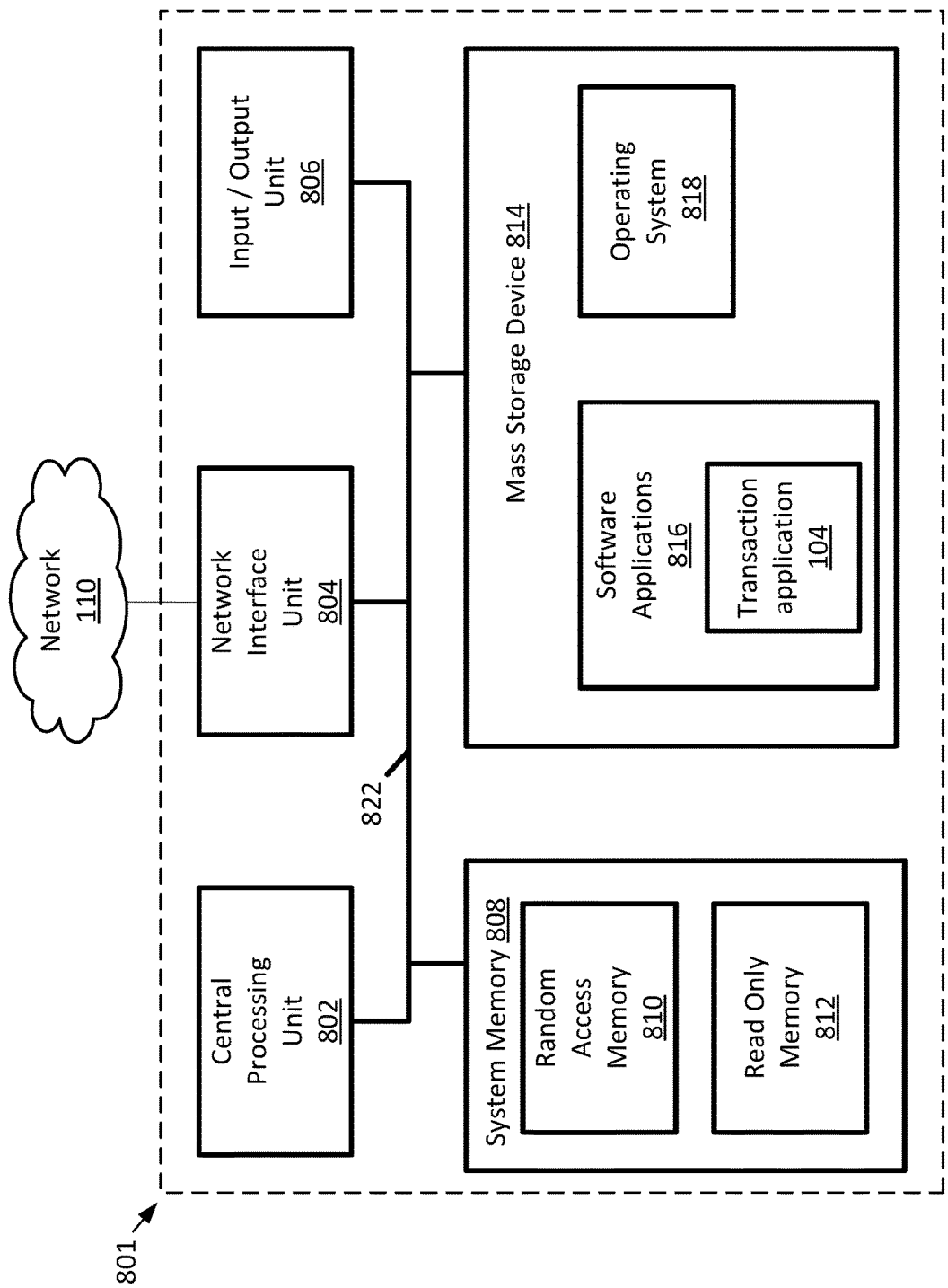
FIG. 7 shows example physical components of a computing device hosting the transaction application shown in FIG. 1.

FIG. 7 shows one example of computing device 801 of the property transaction system 100. As shown, example computing device 801 hosts transaction application 104 that is capable of executing the operations of example process 300. The property transaction system 100 can include different software applications configured to manage communications with other components of system 100 and capable of performing the operations of property transaction system 100 described above.

As illustrated, the example computing device 801 includes at least one central processing unit ("CPU") 802, a system memory 808, and a system bus 822 that couples the system memory 808 to the CPU 802. The system memory 808 includes a random access memory ("RAM") 810 and a read-only memory ("ROM") 812. A basic input/output system that contains the basic routines that help to transfer information between elements within the example computing device 801, such as during startup, is stored in the ROM 812. The example computing device 801 further includes a mass storage device 814. The mass storage device 814 is able to store software applications 816 and data.

The mass storage device 814 is connected to the CPU 802 through a mass storage controller (not shown) connected to the system bus 822. The mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the components in property transaction system 100 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. The network 110 may be a protected network, as discussed above. It should be appreciated that the network interface unit 804 may also be utilized to connect to other types of networks and remote computing systems. The example computing device 801 also includes an input/output unit 806 for receiving and processing input from a number of other devices, including a touch user interface display screen, or another type of input device. Similarly, the input/output unit 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software applications 816, that when executed by the CPU 802, cause the example computing device 801 to provide the functionality of the example computing device 801 discussed herein. For example, the mass storage device 814 and/or the RAM 810 can store software instructions that, when executed by the CPU 802, cause the example computing device 801 to manage property transactions.

Although various embodiments are described herein, those of ordinary skill in the art will understand that many modifications may be made thereto within the scope of the present disclosure. Accordingly, it is not intended that the scope of the disclosure in any way be limited by the examples provided.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The invention claimed is:

1. A portable remote processing apparatus, the apparatus comprising:
a housing;
a processing unit supported by the housing and communicatively connected to a sensor coupled to a heating unit or a cooling unit;
an electronic nose configured to obtain an air sample within a property for sale;
a display unit supported by the housing and connected to the processing unit;
a communication arrangement supported by the housing, including a speaker and a microphone;
a camera supported by the housing; and
system memory, the system memory including instructions that, when executed by the processing unit, cause the apparatus to:
  determine, based on the air sample obtained by the electronic nose, whether at least one of mold, pet dander, evidence of fire, and evidence of smoke is present in the air sample and, based thereon prepare the property for sale for a showing by controlling operation of one or more devices within the property for sale;
  facilitate an appraisal of the property for sale, including to:
    use the camera to capture photographs of the property; and
    use the microphone to record voice notes about aspects of the property;
  facilitate a walk-through of the property for a buyer, including to:
    display the captured photographs of the property using the display unit;
    display status data regarding a status of the property, the status data including data provided to the processing unit by the sensor coupled to the heating unit or the cooling unit;
    playback the recorded voice notes using the speaker; and
    provide information, using the display unit or the communication arrangement, based on a location of the apparatus within the property, the location being determined based upon one or more locating devices positioned within rooms of the property, the locating devices including one or more bar codes or near-field communication tags; and
  negotiate a sale of the property, including to:
    receive, from a device associated with the buyer, an offer to buy the property; and
    send, to the device associated with the buyer, a counteroffer in response to the offer, wherein, after the offer is received and before the counteroffer is sent, no input associated with the offer or the counteroffer is provided by a seller of the property.

* * * * *